United States Patent [19]
Moss et al.

[11] Patent Number: 5,336,190
[45] Date of Patent: Aug. 9, 1994

[54] MEDICAL CASSETTE FOR AMBULATORY MEDICAL INFUSION PUMPS WITH ACCESS PORT FOR RESERVOIR BAGS AND METHOD OF RESUPPLYING BAGS IN SAID CASSETTE

[75] Inventors: Richard Moss, 4928 Panorama Cir., West Bloomfield, Mich. 48323; Fred Erlich, 34536 Quaker Valley, Farmington Hills, Mich. 48331

[73] Assignees: Fred Erlich; Fred Kamienny; Richard Moss

[21] Appl. No.: 106,054

[22] Filed: Aug. 12, 1993

[51] Int. Cl.5 ............................................. A61M 1/00
[52] U.S. Cl. ................................... 604/153; 604/131; 604/151; 604/257; 417/477 A
[58] Field of Search ............... 128/DIG. 12; 604/65, 604/66, 67, 118, 120, 131, 153, 151, 152, 246, 257, 262, 410; 417/474, 475, 476, 477 A, 478, 479

[56] References Cited

U.S. PATENT DOCUMENTS

| D. 232,085 | 7/1974 | Saratoga . | |
|---|---|---|---|
| D. 247,820 | 5/1978 | Stuetzer . | |
| D. 277,980 | 3/1985 | Bransky . | |
| D. 294,733 | 3/1988 | Peterson et al. . | |
| D. 326,153 | 5/1992 | Eastman et al. . | |
| 3,908,657 | 9/1975 | Kowarski | 604/153 |
| 4,187,057 | 2/1980 | Xanthopoulos | 604/153 |
| 4,256,437 | 3/1981 | Brown . | |
| 4,274,407 | 6/1981 | Scarlett . | |
| 4,398,908 | 8/1983 | Siposs . | |
| 4,468,221 | 8/1984 | Mayfield . | |
| 4,559,038 | 12/1985 | Berg et al. . | |
| 4,565,542 | 1/1986 | Berg . | |
| 4,569,674 | 2/1986 | Phillips et al. . | |
| 4,650,469 | 3/1987 | Berg et al. . | |
| 4,667,854 | 5/1987 | McDermott et al. . | |
| 4,845,487 | 7/1989 | Frantz et al. . | |
| 4,886,431 | 12/1989 | Soderquist et al. | 604/153 |
| 4,978,335 | 12/1990 | Arthur, III . | |
| 5,213,483 | 5/1993 | Flaherty et al. . | |

Primary Examiner—C. Fred Rosenbaum
Assistant Examiner—N. Kent Gring
Attorney, Agent, or Firm—Reising, Ethington, Barnard, Perry & Milton

[57] ABSTRACT

A method for resupplying a cassette assembly (14) for an ambulatory medical infusion pump (10) with a new reservoir bag (22a) includes the steps of substantially emptying a used reservoir bag (22) located within said cassette interior (27) of any fluid, supplying an access slot (40) to the interior (27) of the cassette large enough to withdraw the used drug reservoir bag (22) from within the cassette, removing a luer lock (34) located at the end of microbore tubing (32) attached to the reservoir bag, removing the tubing (32) from under a guide retainer (30) in a pumping plate (16) of the cassette, withdrawing the reservoir bag (22) from the access slot (40), inserting a new unused reservoir bag (22a) into the access slot (40) to the interior of said cassette, by inserting a tube (32a) of a new unused reservoir bag and pulling the tube (32a) such that the bag (22a) is pulled through the slot (40) and into the interior (27) of the cassette shell (18).

14 Claims, 2 Drawing Sheets

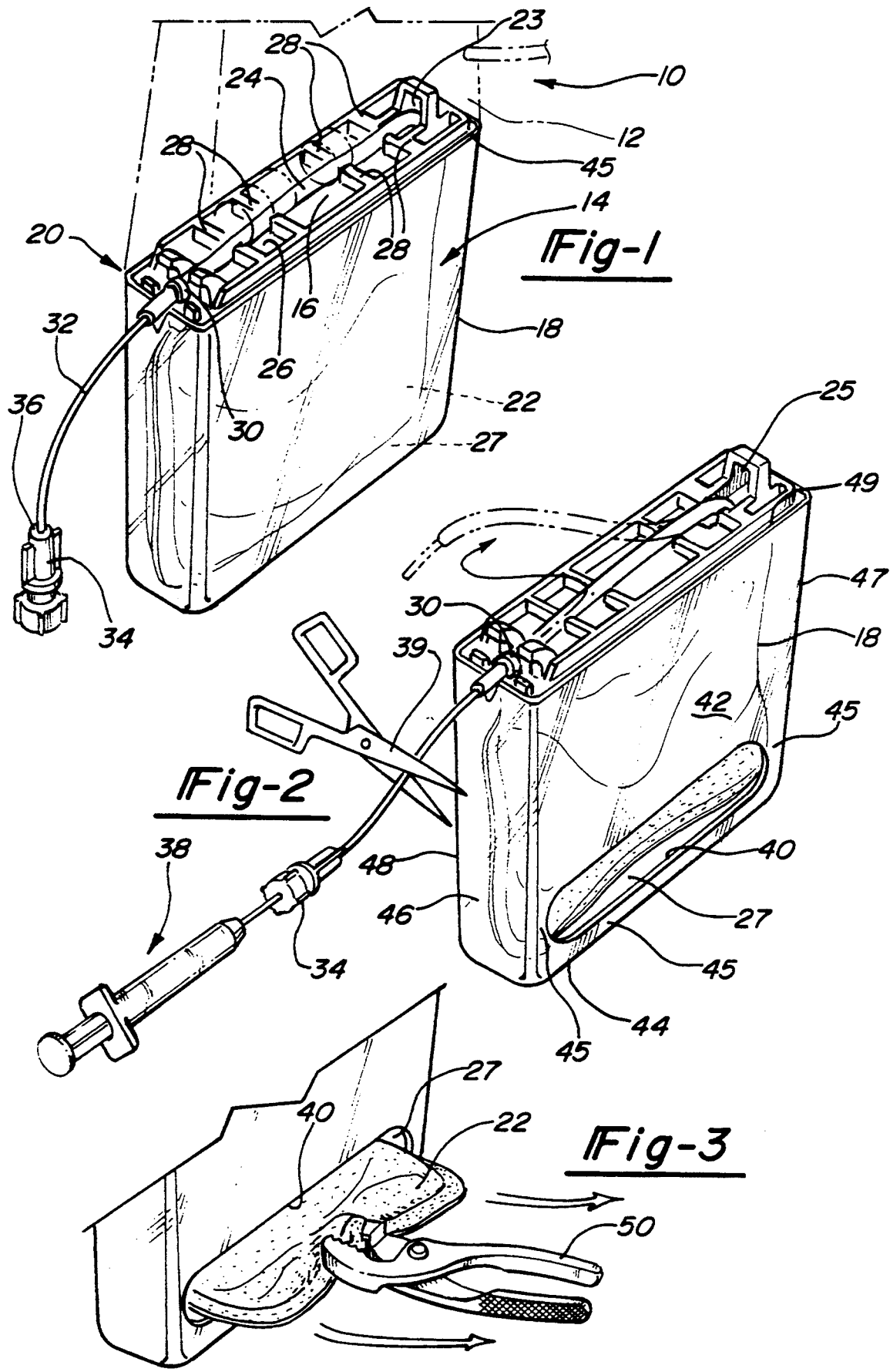

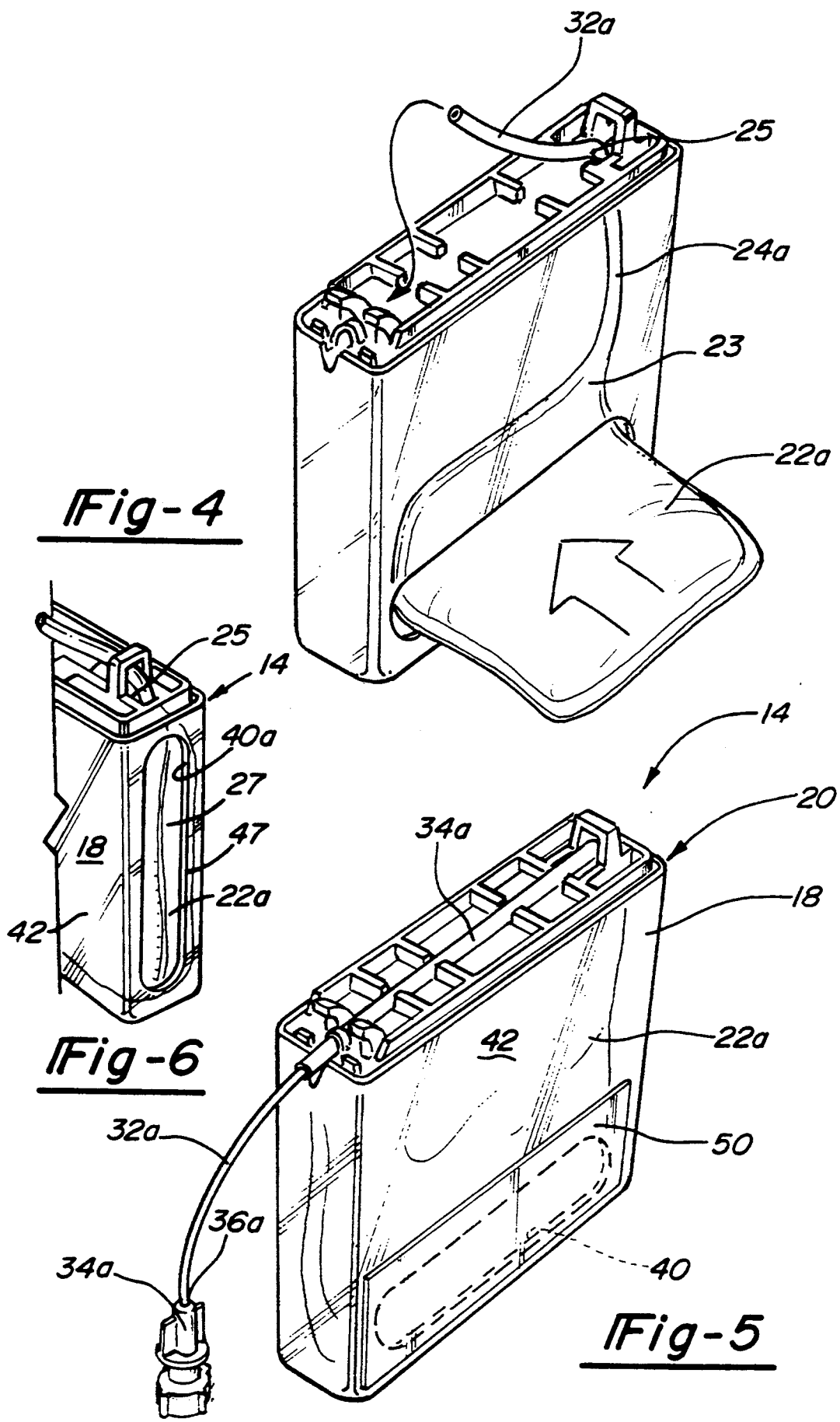

MEDICAL CASSETTE FOR AMBULATORY MEDICAL INFUSION PUMPS WITH ACCESS PORT FOR RESERVOIR BAGS AND METHOD OF RESUPPLYING BAGS IN SAID CASSETTE

TECHNICAL FIELD

The field of this invention relates to a method of refilling and recycling cassettes for ambulatory medical infusion pumps.

BACKGROUND OF THE DISCLOSURE

Ambulatory medical infusion pumps are a commercially successful and popular medical instrument. The pumps allow for the convenient continuous and calibrated delivery of a variety of medicines including but not limited to antibiotics, pain relieving drugs, and chemotherapy drugs.

The pumps have a fastener system that allows a cassette to be removably attached to the pump. A cassette has a soft pliable drug reservoir bag placed within a hard shell cassette made from a rigid plastic such as a poly-carbonate to protect the integrity of the bag. The reservoir bag has a first tube section positioned within the pump assembly on which the pumps presses against the cassette pump plate to draw or pump the medicine out of the bag.

The soft tube section is attached to microbore tubing that exits the pump assembly. The microbore tubing has a luer lock or similar connector attached to its distal end that allows connection to a intravenous infusion or subcutaneous delivery system. The microbore tubing resists any unintentional kinking or crimping thus assuring proper delivery of the drugs therethrough.

The pump plate of the cassette is permanently secured either by adhesive or sonic welding to the cassette shell to assure that the shell is not unintentionally removed from about the bag so that the bag does not become accidentally exposed and maintains its integrity against accidental puncture.

When the medicine infusion is terminated, the one cassette is easily removed. When the medicine needs to be changed, the one cassette is easily removed and another cassette with a second medicine is conveniently attached to the pump.

Because the reservoir bag has been in fluid contact with a patient, the used reservoir bag may contain bodily fluids that passed up though the tubing and into the bag. Thus, the reservoir bag is considered medical waste and must be disposed of accordingly. Many principalities now have laws that forbid medical waste from being placed in landfills. The preferred disposal method is by incineration. For proper incineration, the cassette with both the used reservoir bag and cassette shell need to be incinerated at relatively high temperatures compared to regular incineration temperatures of other waste products. The higher temperatures are needed for the proper decomposition of certain chemotherapy drugs and for certain rigid plastics such as poly-carbonate. The cassette shell is incinerated with the reservoir bag, even though the cassette shell can be easily re-sterilized and capable of storing another reservoir bag.

The pumps are used to deliver small amounts of drugs. A typical reservoir bag is capable of holding only one hundred milliliters (100 ml.). The pump thus can pump many cassettes each day as needed. The pump during its useful life can pump many thousands of cassettes over several years.

The increasing expense and difficulties of proper disposal of the cassette assembly necessitates that only the waste be disposed of and other parts be repaired and reused as possible. The reuse of the cassette shell can save much plastic and reduce the amount of unnecessary incineration and the unwanted particulates and gasses produced by incineration.

SUMMARY OF THE DISCLOSURE

In accordance with one aspect of the invention, a method for resupplying a cassette for an ambulatory medical infusion pump with a new reservoir bag is provided. The method includes the steps of substantially emptying a supply bag located within said cassette of fluid, supplying a access port to the interior of the cassette large enough to withdraw a drug reservoir bag from within the cassette, removing a lock fastener located at the end of a tube attached to the reservoir bag, removing the tube from at least one guide bridge in a pumping plate of the cassette, withdrawing the reservoir bag from the access port, inserting a new unused reservoir bag into the access port to the interior of said cassette, and inserting a tube of a new unused reservoir bag into at least one guide bridge in the cassette plate.

Preferably the port is in a side wall of the cassette. The new unused reservoir bag is preferably inserted into the access port with the tube being inserted first and being pulled again out of the cassette interior to the pumping plate where the tube is pulled to draw any remaining section of the new reservoir bag into the interior of said cassette.

Preferably, the port is resealed after the new reservoir bag is positioned within the cassette with a sheet of adhesive material overlying the access port and adhered to said cassette side wall.

According to another aspect of the invention, a reusable cassette shell for a medical infusion pump system has a cassette assembly removably attachable to a pump housing via a connector system. The cassette assembly has a rigid outer shell including a plate member that is adjacent a squeezable tube of a reservoir bag that is squeezable by a pump in the pump housing. The cassette shell has a wall with an access port therethrough sized and shaped to provide removal of said reservoir bag from an interior of the shell and insertion and installation of a second reservoir bag within the interior of the shell. The cassette shell preferably has the port in a wall being a wall other than said pump plate. The access port is normally closed by a cover placed over said access port. The cover that covers and seals the access port is a removable adhesive sheet attached to the wall containing the access port. The wall is preferably a side wall having a top edge joined with the pump plate. The access port is preferably an elongated vertically disposed slot in the side wall. In another embodiment, an elongated slot is in proximity to a distal bottom wall opposite the pump plate.

BRIEF DESCRIPTION OF THE DRAWINGS

Reference now is made to the accompanying drawings in which:

FIG. 1 is a perspective view of a cassette assembly attachable to a pump (shown in phantom);

FIG. 2 is perspective view of the cassette assembly with the luer lock shown cut off and an access port cut into the side wall of the cassette shell;

FIG. 3 is perspective view similar to FIG. 2 showing the used reservoir bag being removed through the access port;

FIG. 4 is a view similar to FIG. 3 showing a new reservoir bag being inserted into the access port;

FIG. 5 is a view similar to FIG. 4 illustrating the cassette shell having a new reservoir bag positioned therein and an adhesive tape covering the access port; and FIG. 6 is a perspective view of a cassette shell with a different access port.

DETAILED DESCRIPTION OF THE PREFERRED EMBODIMENT

Referring now to FIGS. 1 and 2, an ambulatory medical infusion pump assembly 10 includes a pump housing 12 and a cassette assembly 14 removably attached to the housing 12. The cassette assembly 14 has a pump plate 16 sonically welded to a cassette shell 18 that together forms a casing 20 which contains a flexible reservoir bag 22 at its interior chamber 27. The bag 22 has an upper bag section 23 that is fitted through a tube port 25. A pliable tube 24 is attached to the bag section 23 and is positioned against the exterior side 26 of the pump plate 16. Appropriate guides 28 and tube retainer 30 retain the tube 24 in its proper position against plate 16. The tube 24 is connected to a microbore tubing 32 that extends from the pump housing 12 and cassette casing 20. A Luer lock 34 is connected at the distal end 36 of the microbore tubing 32 to be connected to infusion tubing (not shown).

Referring now particularly to FIG. 2, the cassette assembly 14 is detached from the pump housing 12. If the reservoir bag 22 has any medicine in it, the bag 22 is completely emptied by using a medical syringe 38 being used on luer lock 34. The luer lock 34 is then cut off by scissors 39 and the tubing 24 and 32 is removed out from under the tube retainer 30. An elongated access port 40 i.e. slot is drilled or cut into the side wall 42 of the cassette shell 18. The access port 40 is elongated and in proximity to the bottom 44 of the shell 18. A milling device, router, pin mill or similar device can be used to form the slot 40 in the cassette shell 18. The slot 40 is sized to be large enough to conveniently pull the bag 22 therethrough but is small enough to provide a peripheral edge 45 on side wall 42.

The slot 40 may alternately be located on side walls 46, or edge walls 47 and 48. FIG. 6 illustrates a vertically disposed slot 40a in edge wall 47. Another alternative is to provide that the pump plate 16 is constructed to be removable from the cassette shell 18 to provide access port 40 through the top 49 of the cassette casing 20.

As shown in FIG. 3, the bag 22 is grabbed by a forceps 50 or similar pinching instrument which can be inserted in the slot 40 and clasp the bag 22. Once clasped, the bag 22 is then pulled through the slot 40. The tube 24 and microbore tubing 32 is then pulled through the tube port 25 into the interior 27 and out again through slot 40.

The used bag 22 is then properly disposed as waste. As illustrated in FIGS. 4 and 5, a new unused bag 22a is then inserted into slot 40. The microbore tubing 32a is threaded into the slot 40 and out through the tube port 25. The tubing 32a is then pulled such that the rest of bag 22a is pulled into the interior 27a through slot 40. Once the bag 22a is fully positioned in interior 27, the tubing 32a is then placed under tube retainer 30 and a new Luer lock 34a is then placed on the distal end 36a of the tubing 32a.

Once the new bag 22a is properly positioned in interior 27, a precut adhesive tape 50 of approximately 100 lb. weight is removably attached to the peripheral edge 45 about slot 40 to cover and seal the slot 40.

At this point, the cassette assembly is packaged and sterilized under either standard radiation procedures or ethyleneoxide gas sterilization procedures. In this fashion, a medical cassette shell can be repaired and re-used with a new reservoir bag. Further use of the cassette shell 18 with third and subsequent bags can be accomplished by simply pulling off adhesive tape 50 and pulling out the used bag from slot 40 in the above described fashion and inserting and positioning a new bag in the interior 27 of the cassette shell in the above described fashion. No further milling or drilling of an access slot 40 is necessary after the first bag is replaced.

In this fashion, the need for incinerating the shell after each reservoir bag is emptied is eliminated and the shell may be used with a plurality of sequentially used reservoir bags.

Variations and modifications are possible without departing from the scope and spirit of the present invention as defined by the appended claims.

The embodiments in which an exclusive property or privilege is claimed are defined as follows:

1. A method of resupplying a cassette for an ambulatory medical pump with a supply bag, said method characterized by;
   substantially emptying a supply bag located within said cassette of fluid;
   supplying an access port to the interior of the cassette large enough to withdraw a drug reservoir bag within the cassette;
   removing a lock fastener located at the end of a tube attached to the reservoir bag;
   removing said tube from at least one tube retainer in a pumping plate of said cassette;
   withdrawing the reservoir bag from the port;
   inserting a new unused reservoir bag through said port to the interior of said cassette; and
   inserting a tube of a new unused reservoir bag into said at least one tube retainer.

2. A method as defined in claim 1 further characterized by:
   after said new bag is inserted, covering and sealing said access port.

3. A method as defined in claim 1 further characterized by:
   said port being supplied in a side wall of said cassette.

4. A method as defined in claim 2 further characterized by:
   said new unused reservoir bag being inserted into said port with said tube being inserted first and being pulled again out of said cassette interior to said pumping plate where said tube is pulled to draw any remaining section of said new reservoir bag into said interior of said cassette.

5. A method as defined in claim 3 further characterized by:
   said port being formed in said side wall of said cassette by removing a section of said side wall;
   said new unused reservoir bag being inserted into said port with said tube being inserted first and being pulled again out of said cassette interior to said pumping plate where said tube is pulled to draw any remaining section of said reservoir bag into said interior of said cassette;

after said new reservoir bag is inserted, sealing said port with a sheet of adhesive material overlying said port and adhered to said cassette side wall.

6. A reusable cassette shell for a medical infusion pump system that has a cassette assembly removably attachable to a pump housing via a connector system, said cassette assembly having a rigid outer shell including a plate member that is adjacent a squeezable tube of a reservoir bag that is squeezable by a pump in said pump housing, said cassette shell characterized by:

a wall of said cassette shell has an access port sized and shaped to provide removal of said reservoir bag from an interior of said shell and insertion and installation of a second reservoir bag within said interior of said shell.

7. A cassette shell as defined in claim 6 further characterized by:

said wall being a wall other than said pump plate.

8. A cassette shell as defined in claim 7 further characterized by:

said access port normally being closed by a cover placed over said access port.

9. A cassette shell as defined in claim 8 further characterized by:

said cover that closes said access port is a adhesive sheet removably attached to said wall containing said access port.

10. A cassette shell as defined in claim 7 further characterized by:

said wall being a side wall having a top edge joined with said pump plate.

11. A cassette shell as defined in claim 10 further characterized by:

said access port being an elongated slot in said side wall in proximity to a distal bottom wall opposite said pump plate.

12. A cassette shell as defined in claim 11 further characterized by:

said access port normally being closed by a cover placed over said access port.

13. A cassette shell as defined in claim 12 further characterized by:

said cover that seals said access port is a removable adhesive sheet attached to said wall containing said access port.

14. A cassette shell as defined in claim 10 further characterized by:

said access port being an elongated vertically disposed slot in said side wall.

* * * * *